United States Patent [19]

Flaum

[11] Patent Number: 6,097,184

[45] Date of Patent: Aug. 1, 2000

[54] NUCLEAR MAGNETIC RESONANCE WELL LOGGING TO DETERMINE GAS-FILLED POROSITY AND OIL-FILLED POROSITY OF EARTH FORMATIONS WITHOUT A CONSTANT STATIC MAGNETIC FIELD GRADIENT

[75] Inventor: Charles Flaum, Ridgefield, Conn.

[73] Assignee: Schlumberger Technology Corporation, Ridgefield, Conn.

[21] Appl. No.: 09/001,896

[22] Filed: Dec. 31, 1997

[51] Int. Cl.$^7$ ...................................................... G01V 3/00
[52] U.S. Cl. .............................................................. 324/303
[58] Field of Search ............................................. 324/303

[56] References Cited

U.S. PATENT DOCUMENTS

| | | | |
|---|---|---|---|
| 5,023,551 | 6/1991 | Kleinberg et al. | 324/303 |
| 5,055,788 | 10/1991 | Kleinberg et al. | 324/303 |
| 5,153,514 | 10/1992 | Griffin et al. | 324/303 |
| 5,212,447 | 5/1993 | Paltiel | 324/300 |
| 5,291,137 | 3/1994 | Freedman | 324/300 |
| 5,680,043 | 10/1997 | Hurlimann et al. | 324/303 |
| 5,796,252 | 8/1998 | Kleinberg et al. | 324/303 |
| 5,936,405 | 8/1999 | Prammer et al. | 324/303 |

OTHER PUBLICATIONS

Flaum, C., Kleinberg, R., and Hurlimann, M., Identification Of Gas With The Combinable Magnetic Resonance Tool (CMR*), Paper L. SPWLA, 37th Annual Logging Symposium, New Orleans, Jun. 16–19, 1996.

Akkurt, R., Vinegar H.J., Tutunjian, P.N., and Guillory, A.J., 1995, NMR Logging Of Natural Gas Reservoirs, Paper N. SPWLA 36th Annual Logging Symposium, Paris.

Prammer, M.G., Mardon, D., Coates, G.R., and Miller, M.N., 1995, Lithology–Independent Gas Detection by Gradient–NMR Logging, SPE No. 30562, SPE 70th Annual Technical Conference, Dallas.

Freedman, R. and Morriss, C.E., 1995 Processing Of Data From An NMR Logging Tool, SPE 30560, SPE 70th Annual Technical Conference, Dallas.

E. Fordham et al., "Imaging Multiexponential Relaxation In the (y, $\log_e T_1$) Plane With Application To Clay Filtration In Rock Cores", Journal Of Magnetic Resonance, 1995.

*Primary Examiner*—Christine K. Oda
*Assistant Examiner*—Tiffany A. Fetzner
*Attorney, Agent, or Firm*—William B. Batzer; Martin M. Novack

[57] ABSTRACT

A technique is disclosed for determining the gas-filled porosity and oil-filled porosity in a region of investigation of earth formations surrounding a borehole including the following steps: (a) providing a logging device that is moveable through the borehole; (b) generating, from the logging device, a static magnetic field in the region of investigation of the formations, the static field having a magnetic field gradient that is not constant in the region of investigation; (c) determining the gradient distribution of the static magnetic field in the region of investigation, and determining a first function of the gradient distribution and the diffusion coefficient of oil, and a second function of the gradient distribution and the diffusion coefficient of gas; (d) generating a first sequence of magnetic field pulses in the region of investigation of the formations using a first wait time, and detecting a first sequence of nuclear magnetic resonance spin echoes from the formations; (e) generating a second sequence of magnetic field pulses in the region of investigation of the formations using a second wait time, and detecting a second sequence of nuclear magnetic resonance spin echoes from the formations; (f) producing, from differences of respective echoes of the second and first sequences of spin echoes, an echo difference signal; and (g) determining the gas-filled porosity and oil-filled porosity in the region of investigation of earth formations from: the echo difference signal, a response function which depends on the first function, and a response function which depends on the second function.

39 Claims, 10 Drawing Sheets

NUCLEAR MAGNETIC RESONANCE WELL LOGGING TO DETERMINE GAS-FILLED POROSITY AND OIL-FILLED POROSITY OF EARTH FORMATIONS WITHOUT A CONSTANT STATIC MAGNETIC FIELD GRADIENT

FIELD OF THE INVENTION

This invention relates to apparatus and techniques for determining characteristics of earth formations surrounding a borehole and, more particularly, to an apparatus and method for nuclear magnetic resonance borehole logging to identify and characterize hydrocarbons, such as by detecting the presence of gas and/or by determining the volumes of gas and oil in a region of the formations.

BACKGROUND OF THE INVENTION

General background of nuclear magnetic resonance (NMR) well logging is set forth in copending U.S. patent application Ser. No. 08/873,582, assigned to the assignee hereof, and in U.S. Pat. No. 5,023,551. Briefly, in NMR operation the spins of nuclei align themselves along an externally applied static magnetic field. This equilibrium situation can be disturbed by a pulse of an oscillating magnetic field (e.g. an RF pulse), which tips the spins away from the static field direction. After tipping, two things occur simultaneously. First, the spins precess around the static field at the Larmor frequency, given by $\omega_0 = \gamma B_0$, where $B_0$ is the strength of the static field and $\gamma$ is the gyromagnetic ratio. Second, the spins return to the equilibrium direction according to a decay time T1, the spin lattice relaxation time. For hydrogen nuclei, $\gamma/2\pi = 4258$ Hz/Gauss, so, for example, for a static field of 235 Gauss, the frequency of precession would be 1 MHz. Also associated with the spin of molecular nuclei is a second relaxation, T2, called the spin-spin relaxation time. At the end of a ninety degree tipping pulse, all the spins are pointed in a common direction perpendicular to the static field, and they all precess at the Larmor frequency. However, because of small inhomogeneities in the static field due to imperfect instrumentation or microscopic material heterogeneities, each nuclear spin precesses at a slightly different rate. T2 is a time constant of this "dephasing".

A widely used technique for acquiring NMR data both in the laboratory and in well logging, uses an RF pulse sequence known as the CPMG (Carr-Purcell-Meiboom-Gill) sequence. As is well known, after a wait time that precedes each pulse sequence, a ninety degree pulse causes the spins to start precessing. Then a one hundred eighty degree pulse is applied to keep the spins in the measurement plane, to cause the spins which are dephasing in the transverse plane to reverse direction and to refocus. By repeatedly reversing the spins using one hundred eighty degree pulses, a series of "spin echoes" appear, and the train of echoes is measured and processed.

Identification of the presence of gas in a formation is one of the most important tasks of petrophysical log interpretation. Since NMR is a proton measurement, it is somewhat analogous to the porosity measurement with a neutron tool; namely, it is sensitive to the hydrogen index of the formation, which is significantly reduced in gas. However, unlike the neutron tool, the NMR measurement is insensitive to neutron absorbers, crystalline waters of hydration, and lithology. A so-called "Amplitude Method" takes advantage of this to evaluate the gas volume of the formation. The Amplitude Method is summarized, for example, in Flaum, C., Kleinberg, R., and Hurlimann, M., Identification Of Gas With The Combinable Magnetic Resonance Tool (CMR), Paper L. SPWLA, 37th Annual Logging Symposium, New Orleans, Jun. 16–19, 1996.

Recently, much attention has been focused on a secondary phenomenon which can be exploited to use NMR for an independent indication of gas; namely, diffusion. Exploitation of the diffusion process is based on the fact that molecular diffusion is more rapid in gas than in water or most liquid hydrocarbons.

Diffusion can have a significant effect on the pulsed NMR measurement, since a diffusing molecule with a polarized proton can be displaced an appreciable distance between successive pulses. If the static magnetic field is not uniform, this displacement will cause a dephasing of the transverse magnetization. The result is a noticeable decrease in the relaxation time $T_2$, or a shift in the $T_2$ distribution spectrum to shorter times.

Among the techniques that have been suggested for obtaining gas-related measurements are techniques known as Differential Spectrum, Shifted Spectrum, Matched Filter, and Echo Ratio methods.

The Differential Spectrum Method (DSM) involves acquiring a difference between $T_2$ distributions at two different polarization times, taking advantage of long $T_1$ relaxation time of the gas. [Reference can be made to R. Akkurt et al., NMR Logging of Natural Gas Reservoirs, Paper N, SPWLA 36th Annual Logging Symposium, 1995.] The observed difference reflects the change in the amount of polarization of the gas phase, while signal from the water phase is canceled out. The oil phase, if it is present, may contribute to and distort the result.

The Shifted Spectrum Method (SSM) takes advantage of the large diffusion coefficient of the gas phase. [Reference can again be made to Akkurt et al., supra.] It involves acquiring a difference between $T_2$ distributions at two different echo spacings, since diffusion effect is sensitive to echo spacing. Signal from non-diffusing components cancels out in the difference, and the remainder is an "S" shaped distribution from the gas phase. A limitation of this technique is that the details of the shape of $T_2$ distributions may be affected by factors other than gas presence.

The Echo Ratio Method (ERM) is an improvement over SSM, in that the difference is obtained in the time domain, avoiding certain distortions that occur when transforming from time domain to $T_2$ domain. [Reference can be made, for example, to C. Flaum et al., Identification Of Gas With Combinable Magnetic Resonance Tool ("CMR"), 1996, supra, and to the above-referenced copending U.S. patent application Ser. No. 08/873,582. ] A limitation of this technique is that the residual signal is small, and it is necessary to compare signals at different echo spacings.

The Matched Filter Method (MFM) is a combination of DSM and SSM, but the difference is obtained in the time domain, and the result is fitted to one or two "basis functions" (filters) to obtain volumes of gas or oil and gas. [Reference can be made to M. G. Prammer et al., Lithology-Independent Gas Detection By Gradient-NMR Logging, Society Of Petroleum Engineers, SPE 30562, 1995.] The water signal cancels out. The general method involves two sets of data with different wait times and different echo spacings. The method does rely on a priori knowledge of the properties (bulk T2 relaxation times and diffusion coefficients of the oil and gas phases).

An application of MFM involves two data sets with largely contrasting wait times ($T_W$) but the same (relatively long, e.g. 1 ms) echo spacings ($T_E$). In this method, the water signal cancels out, and the gas and oil signals are widely separated in $T_2$ space due to large contrast in diffusion in the two phases. A mere presence of signal at low $T_2$ is already a gas indication. A matched filter fit to the echo difference yields a quantitative answer. The matched filters, or response functions, for this case would be:

$$f(t)_{oil} = [e^{-T_{W1}/T_{1\text{-}oil}} - e^{-T_{W2}/T_{1\text{-}oil}}]e^{-t/T^*_{2\text{-}oil}} \quad (1a)$$

$$f(t)_{gas} = HI_{gas}[e^{-T_{W1}/T_{1\text{-}gas}} - e^{-T_{W2}/T_{1\text{-}gas}}]e^{-t/T^*_{2\text{-}gas}} \quad (1b)$$

where $T_{W1}$ and $T_{W2}$ are the respective wait times, $T_{1\text{-}oil}$ and $T_{1\text{-}gas}$ are the spin lattice relaxation times of bulk oil and gas, respectively, $HI_{gas}$ is the hydrogen index of the gas, and the asterisk on $T_2$'s indicates that it is affected by diffusion, as given by the equation:

$$1/T^*_2 = 1/T_{2\text{-}bulk} + 1/T_{2\text{-}D} \quad (2)$$

$T_{2\text{-}D}$ is a known function of diffusion coefficient and echo spacing.

It has been generally understood that the foregoing MFM technique requires use of an NMR logging tool having a constant gradient of static magnetic field. A constant gradient implies a constant diffusion effect. In $T_2$ space, the gas signal will be shifted by diffusion, but still appear as a narrow peak in a constant gradient. In NMR logging devices with a broad magnetic field gradient distribution [see, for example, the type of logging device disclosed in U.S. Pat. No. 5,055,788], the gas signal in $T_2$ space will be significantly broadened by diffusion, presumably making it difficult, if not impossible, to identify, especially in the presence of normal noise.

It is among the objects of the present invention to overcome limitations of prior art NMR techniques for detecting and characterizing hydrocarbons in earth formations.

SUMMARY OF THE INVENTION

In accordance with a feature of the present invention, measurements from a logging device that does not have a constant static magnetic field gradient, and indeed may have a broad gradient distribution, are used in a matched filter technique for detecting and characterizing hydrocarbons in earth formations. Since the diffusion and transverse relaxation processes are largely independent, the separability in $T_2$ space and the ability to perform matched filtering can be recovered by a transformation of the response functions and/or the data. To see how this can be done, consider the general expression for measured echo trains as a function of time:

$$A(t, T_E, D) = A_0 \int_0^\infty B(T_2) e^{-t/T_2} dT_2 \int J(G) e^{-(G^2 \gamma^2 T_E^2 Dt/12)} dG \quad (3)$$

where:
$A_0$ = amplitude at time=0, proportional to initial polarization.
t = time, sec
$T_E$ = echo spacing, sec
D = effective diffusion coefficient, $cm^2$/sec
G = magnetic field gradient, gauss/cm
J(G) = magnetic field gradient distribution, cm/gauss
$T_2$ = relaxation time, sec
$B(T_2)$ = $T_2$ distribution, 1/sec
$\gamma$ = proton gyromagnetic ratio, = $2\pi^*4258$/gauss-sec.

The first integral in eq. (3) is the standard $T_2$ expansion. The second is an integral over the gradient distribution, and when the gradient is a constant, this second integral reduces to a simple exponential. When the gradient is not a constant, an approach hereof is to map the static magnetic field gradient, such as by mapping and verification with bench-top measurements with a water bottle. [Reference can be made, for example, to the above-referenced copending U.S. patent application Ser. No. 08/873,582 and to the publication of C. Flaum et al., supra, with regard to mapping of a complex static magnetic field gradient.] The second integral can then be replaced by a known function, F(t,D). An analog of eq. (1) can now be written in a general way:

$$f(t)_{oil} = [e^{-T_{W1}/T_{1\text{-}oil}} - e^{-T_{W2}/T_{1\text{-}oil}}]e^{-t/T_{2\text{-}oil}}F(t, D_{oil}) \quad (4a)$$

$$f(t)_{gas} = HI_{gas}[e^{-T_{W1}/T_{1\text{-}gas}} - e^{-T_{W2}/T_{1\text{-}gas}}]e^{-t/T_{2\text{-}gas}}F(t, D_{gas}) \quad (4b)$$

where the $T_2$ values are now the bulk values, and the diffusion is handled explicitly in F. The acquired echo difference can now be fit to the above functions using a weighted least squares fitting procedure of type well known various scientific applications.

Furthermore, if the measured echo amplitude differences are modified using:

$$A^*(t) = A(t)/F(t, D_{gas}) \quad (5)$$

and transformed into $T_2$ space, it can be seen from eq. (4), that the gas phase will now appear as a narrow peak in the $T_2$ distribution, as its bulk value. Because the oil phase has a much lower diffusion coefficient, D, the oil signal will be pushed into much higher $T_2$ values by this transformation, thereby separating it from the gas signal, so that the presence or absence of gas can be detected.

In another form of the invention, the echo spacing can be varied. In this case, F is function of $T_E$ as well as t and D, and transformation functions and response functions for gas, oil and water are used.

In accordance with an embodiment of the method of the invention, there is disclosed a technique for determining the gas-filled porosity and oil-filled porosity in a region of investigation of earth formations surrounding a borehole that includes the following steps: (a) providing a logging device that is moveable through the borehole; (b) generating, from the logging device, a static magnetic field in the region of investigation of the formations, the static field having a magnetic field gradient that is not constant in the region of investigation; (c) determining the gradient distribution of the static magnetic field in the region of investigation, and determining a first function of the gradient distribution and the diffusion coefficient of oil, and a second function of the gradient distribution and the diffusion coefficient of gas; (d) generating, from the logging device, a first sequence of magnetic field pulses in the region of investigation of the formations using a first wait time, and detecting a first sequence of nuclear magnetic resonance spin echoes from the formations; (e) generating, from the logging device, a second sequence of magnetic field pulses in the region of investigation of the formations using a second wait time, and detecting a second sequence of nuclear magnetic resonance spin echoes from the formations; (f) producing, from differences of respective echoes of the second and first sequences of spin echoes, an echo difference signal; and (g) determining the gas-filled porosity and oil-filled porosity in the region of investigation of earth formations from: the echo difference signal, a response function which depends on the first function, and a response function which depends on the second function.

In a preferred embodiment of this form of the invention, the first wait time is a relatively short wait time, and the second wait time is a relatively long wait time, the second wait time being more than twice said first wait time. In this embodiment, the step of determining gas-filled porosity and oil-filled porosity comprises fitting the echo difference signal to the response function which depends on the second function and the response function which depends on the first function. Also in this embodiment, the response function which depends on the first function also depends on the spin lattice relaxation time of bulk oil, and the response function which depends on the second function also depends on the spin lattice relaxation time of bulk gas.

In accordance with another embodiment of the method of the invention, there is a disclosed a method for detecting the presence of gas in a region of investigation of earth formations surrounding a borehole that includes the following steps: (a) providing a logging device that is moveable through the borehole; (b) generating, from the logging device, a static magnetic field in the region of investigation of the formations, the static field having a magnetic field gradient that is not constant in the region of investigation; (c) determining the gradient distribution of the static magnetic field in the region of investigation, and determining a first function of the gradient distribution and the diffusion coefficient of gas; (d) generating, from the logging device, a first sequence of magnetic field pulses in the region of investigation of the formations using a first wait time, and detecting a first sequence of nuclear magnetic resonance spin echoes from the formations; (e) generating, from the logging device, a second sequence of magnetic field pulses in the region of investigation of the formations using a second wait time, and detecting a second sequence of nuclear magnetic resonance spin echoes from the formations; (f) producing, from differences of respective echoes of the first and second sequences of spin echoes, an echo difference signal; (g) modifying the echo difference signal with the first function to produce a modified echo difference signal; (h) converting the modified echo difference signal into a $T_2$ distribution, where $T_2$ is spin-spin relaxation time; and (i) detecting the presence of gas in the region of investigation of earth formations from the $T_2$ distribution.

In the described embodiments, the existence of a non-constant gradient of the static magnetic field of an NMR logging apparatus is shown to not be an impediment to detecting the presence of gas and/or determining gas-filled porosity of formations surrounding a borehole. A further advantage of the present technique is as follows: In a broad distribution of gradients, some relatively high gradient values can be present, with accompanying greater sensitivity to diffusion and gas presence.

Further features and advantages of the invention will become more readily apparent from the following detailed description when taken in conjunction with the accompanying drawings.

DETAILED DESCRIPTION

Figure 1:
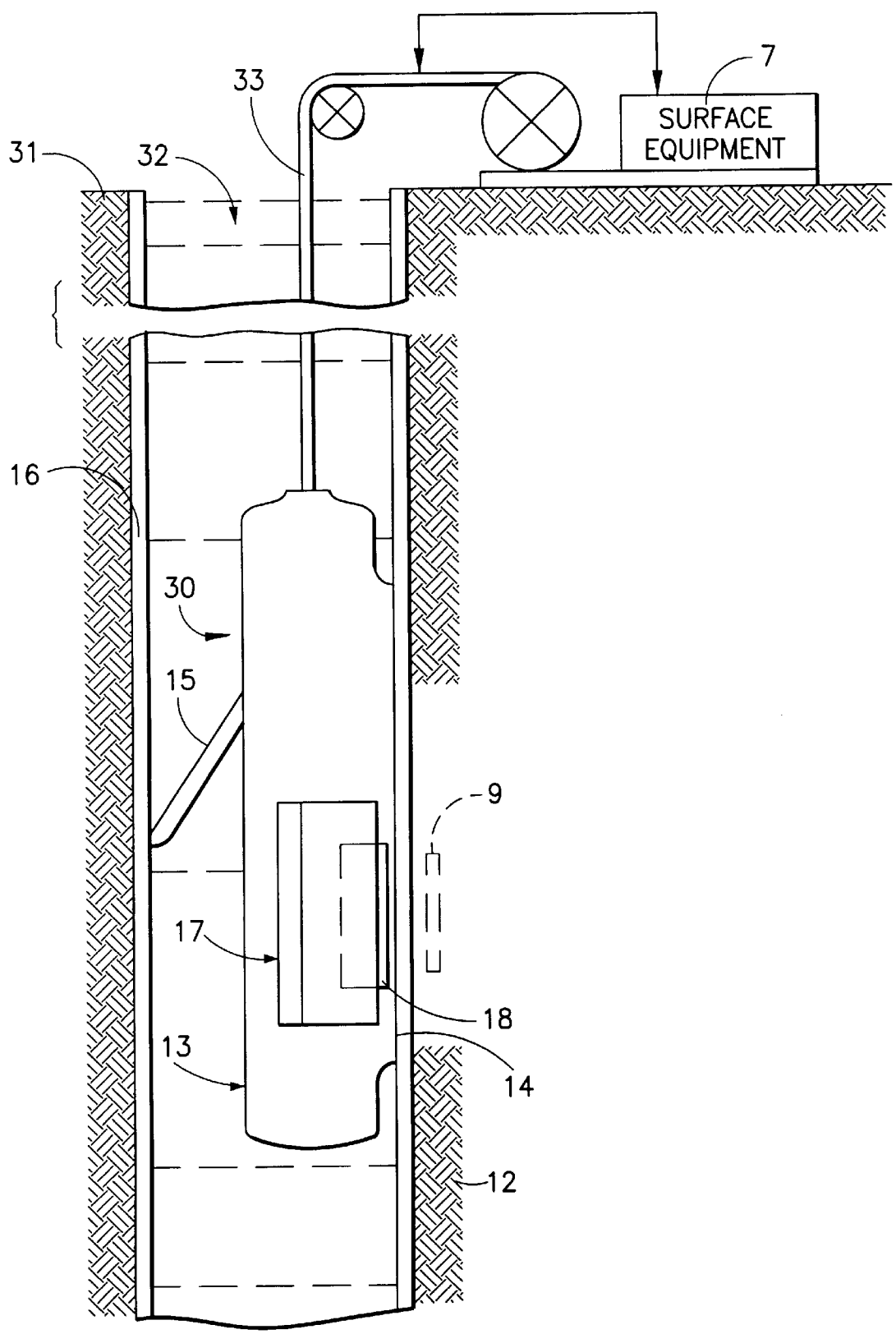
FIG. 1 is a diagram, partially in block form, of a prior art nuclear magnetic resonance logging apparatus which can be configured to in practice embodiments of the invention.

Referring to FIG. 1, there is shown an apparatus for investigating subsurface formations 31 traversed by a borehole 32, which can be used in practicing embodiments of the invention. The borehole 32 is typically, although not necessarily, filled with a drilling fluid or mud which contains finely divided solids in suspension, and mudcake 16 is shown on the walls of the borehole.

An investigating apparatus or logging device 30 is suspended in the borehole 32 on an armored cable 33, the length of which substantially determines the relative depth of the device 30. The cable length is controlled by suitable means at the surface such as a drum and winch mechanism (not shown). Surface equipment, represented at 7, can be of conventional type, and can include a processor subsystem and communicates with the downhole equipment. As described in the U.S. Pat. No. 5,055,788, the device 30 has a face 14 shaped to intimately contact the borehole wall, with minimal gaps or standoff, and a retractable arm 15 which can be activated to press the body of the tool 13 against the borehole wall during a logging run, with the face 14 pressed against the wall's surface. Although the tool 13 is shown as a single body, the tool may alternatively comprise separate components such as a cartridge, sonde or skid, and the tool may be combinable with other logging tools. Also, while a wireline is illustrated, alternative forms of physical support and communicating link can be used, for example in a measurement while drilling system.

Figure 5B:
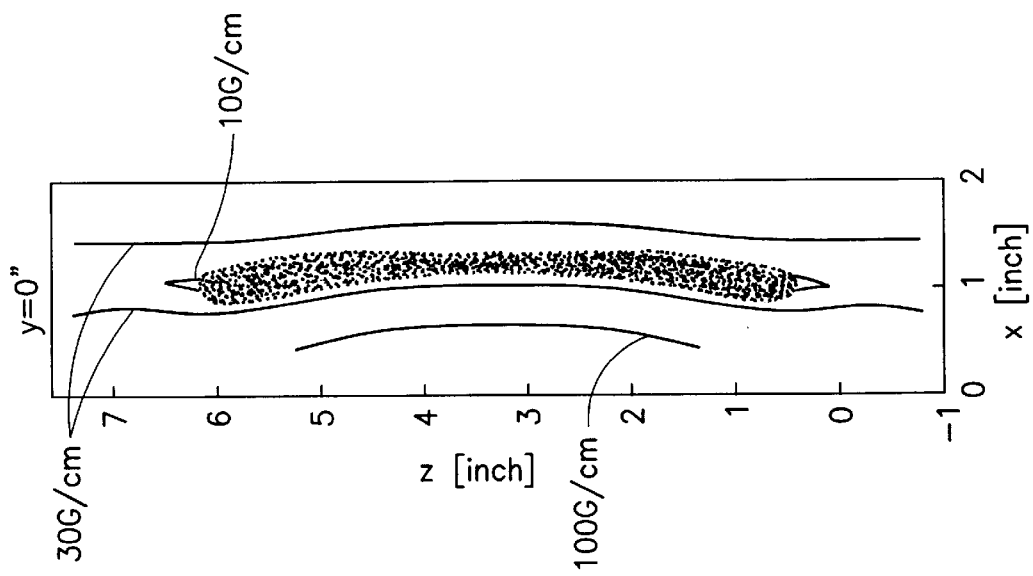
FIGS. 5A and 5B are maps showing the static magnetic field strength and field gradient in an investigation region of a logging tool, as taken through respective cross-sections. The contour lines of constant gradients correspond to 3 G/cm, 10 G/cm, 30 G/cm, 100 G/cm, and 300 G/cm, respectively.
Figure 5A:
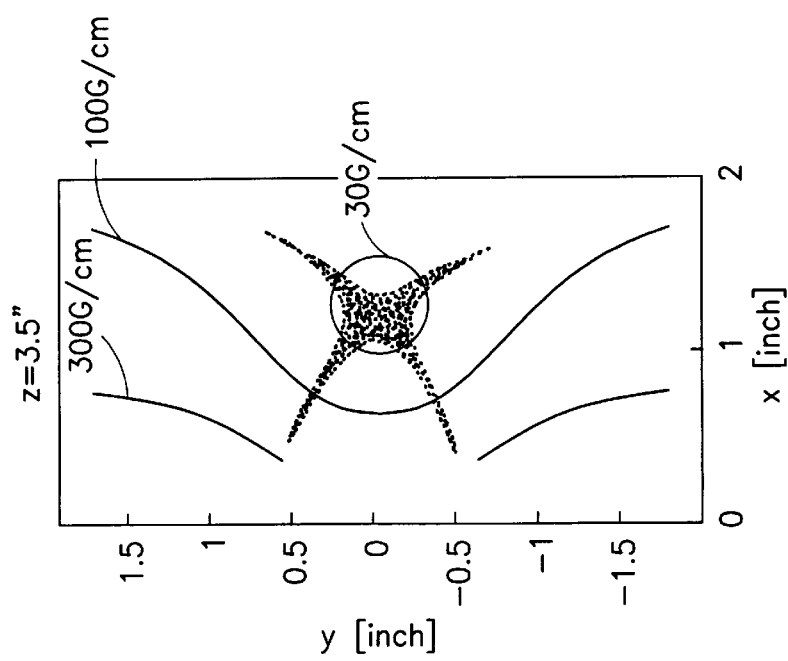

The logging device 30 includes a magnet array 17 and an RF antenna 18 positioned between the array 17 and the wall engaging face 14. Magnet array 17 produces a static magnetic field $B_0$ in regions surrounding the tool 13. The antenna 18 produces, at selected times, an oscillating magnetic field $B_1$ which is focussed into downhole formation 12, and is superposed on the static field $B_0$ within those parts of formation opposite the face 14. The "volume of investigation" a of the tool, shown in dotted lines in FIG. 1, is a vertically elongated region directly in front of tool face 14 in which there is a point at which the magnetic field produced by the magnet array 17 has a spatial gradient which is approximately zero. However, there are substantial non-constant magnetic field gradients in the investigation region, especially near the periphery thereof. FIGS. 5A and 5B show the static magnetic field gradient in the investigation region of a typical device of the type described in the '788 Patent. As described in the referenced Patent, the tool 13 can make measurements by magnetically tipping the nuclear spins of particles in formation 12 with a pulse of oscillating field $B_1$, and then detecting the precession of the tipped particles in the static, homogeneous field $B_0$ within the volume of investigation over a period of time.

Figure 2:
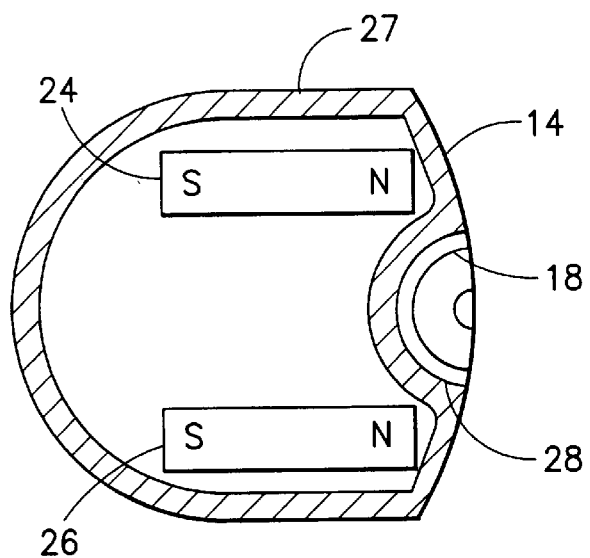
FIG. 2 is a cross-sectional diagram of a portion of the FIG. 3 nuclear magnetic resonance logging apparatus.

FIG. 2 shows a magnet array 17 of the type disclosed in an embodiment of the referenced '788 Patent. The magnet array includes two permanent magnets 24 and 26, which are mounted generally parallel to each other within a metal alloy body 27. The body 27 should be of a material having low magnetic permeability, so as to not interfere with the static magnetic field. Magnets 24 and 26 are slabs which are elongated in the longitudinal direction of the borehole. The magnetic poles of each magnet are not on the smallest faces of the slab, commonly viewed as the ends of a bar magnet. Instead, the poles appear on the two opposing edges of the slab magnet and point to the left and right, respectively, in the Figure. Therefore, within the formation 12, the magnetic field $B_0$ surrounding the magnets remains fairly constant along the longitudinal direction of the borehole axis. In the illustration of FIG. 2, magnets 24, 26 are symmetrically mounted in the two sides of the body 27 with the north poles facing the same direction, that is, the direction of the face 14 of the tool. One or more further permanent magnets can be used.

Figure 3:
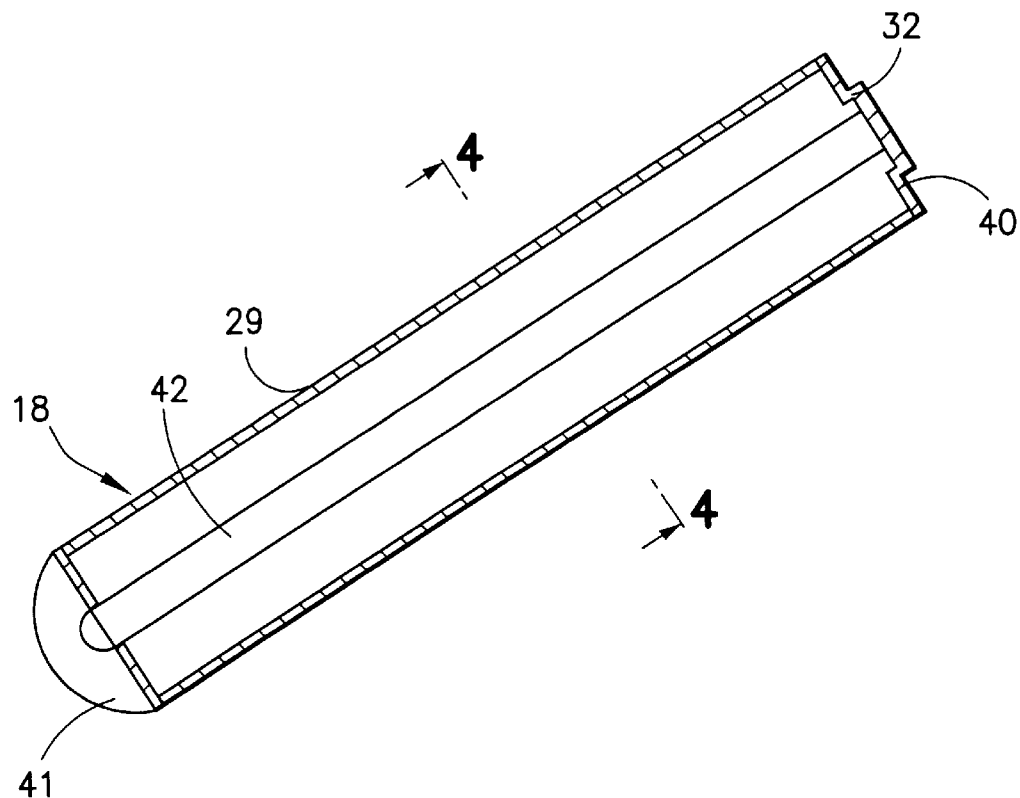
FIG. 3 is a perspective view of the RF antenna of the FIG. 3 nuclear magnetic resonance logging apparatus.
Figure 4:
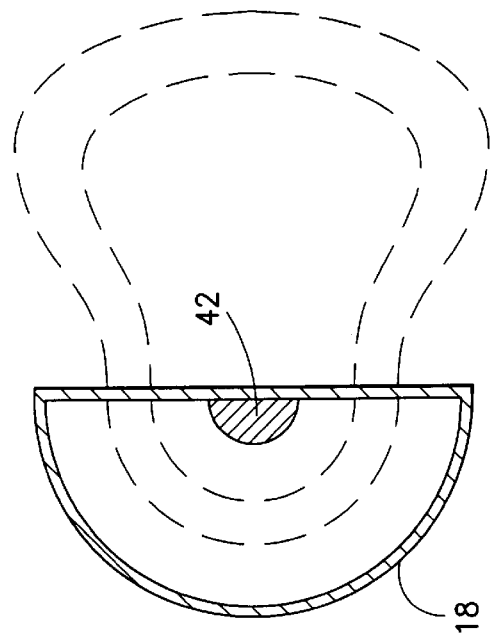
FIG. 4 is a cross-sectional view of the RF antenna of FIG. 3, as taken through a section defined by the arrows 4—4 in FIG. 3.

As described in the referenced '788 Patent, the metal body 27 has, on the front face 14 thereof, a semi-cylindrically shaped cavity or slot 28 which faces formations engaged by the face 14. The cavity 28 is adapted for receiving an RF antenna 18 that is shown in FIGS. 3–4. The antenna 18 is positioned outside of the metal body 27 (FIG. 2) of the tool, and is thereby shielded from electromagnetic communication with regions of the borehole which lie behind the body 27, or regions of other formations in directions intercepted by the body 27. Antenna 18 is thus responsive only to magnetic fields originating in front of the wall engaging face 14, e.g. fields originating in the formation 12 or in the mudcake or mud which contacts face 14 in the vicinity of the antenna 18. In a disclosed embodiment of the referenced Patent, the body 27 is made of metal alloy sheathing, rigidly attached to interior metal bracing, which envelops most components of the tool other than the antenna 18, including the circuitry, the magnet array 17, and the hydraulics system of the arm 15. The Patent points out that the body 27 can alternatively be constructed of other materials, so long as the overall structure is sufficiently strong and the magnetic field of the magnet array 17 can penetrate the body and enter the adjoining formation 12.

In the referenced '788 Patent, the antenna 18 is used both as an RF transmitter to produce an oscillating magnetic field in the formations, and as a receiving antenna to detect coherent magnetic signals emanating from precessing protons (spins) after the oscillating field is terminated. The antenna, which has a body 29 and an elongated center probe 42, across which signals are applied and detected, serves effectively as a current loop which produces an oscillating magnetic field $B_1$ (see FIG. 4) within the volume of investigation that is perpendicular to the static magnetic field, $B_0$ (which is radial in the volume of investigation). The body 29 is trough-shaped and has end plates 40, 41 with the center conductor or probe 42 extending from one end plate 40 to the other end plate 41, parallel to and centered in the semi-cylindrical trough 29. The U.S. Pat. No. 5,153,514 discloses that the trough antenna, which can be filled with a ferrite, can have an inner conductive shell that is separated from a steel body by a rubber layer, which suppresses magnetoacoustic ringing. It will be understood that various other types of NMR logging equipment with a non-constant gradient in the static magnetic field can be used in practicing the invention.

Figure 6:
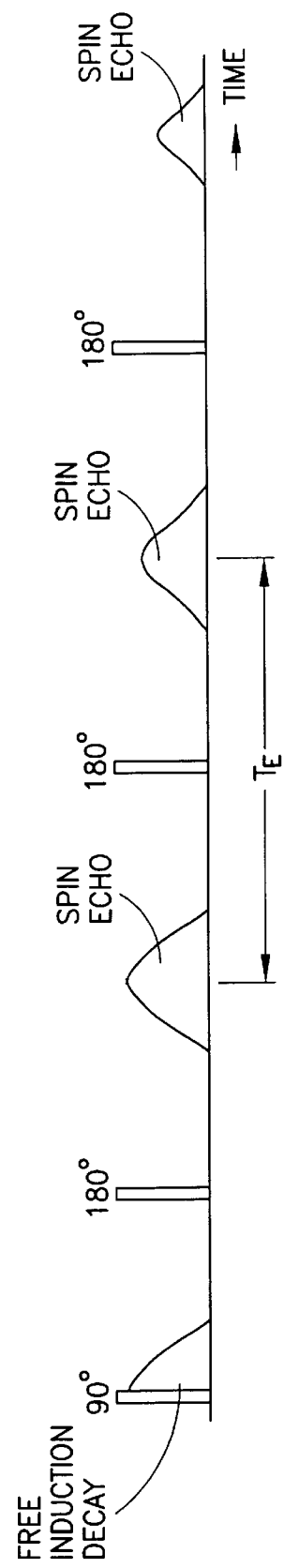
FIG. 6 is a diagram of an embodiment of a nuclear magnetic resonance pulse sequence that can be used in an embodiment of the invention.

In an example of an embodiment hereof, the pulse sequence used can be a conventional type of Carr Purcell or CPMG sequence as illustrated in FIG. 6. However, it will be understood that any other suitable type of pulse sequence can be used, consistent with the principles hereof.

In an embodiment hereof, a matched filter fit to a difference of echo trains is utilized. As first summarized above, the matched filters or response functions are:

$$f(t)_{oil} = [e^{-T_{W1}/T_{1-oil}} - e^{-T_{W2}/T_{1-oil}}]e^{-t/T_{2-oil}}F(t, D_{oil}) \quad (4a)$$

$$f(t)_{gas} = HI_{gas}[e^{-T_{W1}/T_{1-gas}} - e^{-T_{W2}/T_{1-gas}}]e^{-t/T_{2-gas}}F(t, D_{gas}) \quad (4b)$$

where $F(t, D_{oil})$ and $F(t, D_{gas})$ are given by $$F(t, D_{oil}) = \int J(G) \, e^{-(G^2\gamma^2 T_E^2 D_{oil} t/12)} dG \quad (6a)$$

$$F(t, D_{gas}) = \int J(G) \, e^{-(G^2\gamma^2 T_E^2 D_{gas} t/12)} dG \quad (6b)$$

where:
t=time, sec
$T_E$ echo spacing, sec
$D_{oil}$=effective diffusion coefficient of oil, cm$^2$/sec
$D_{gas}$=effective diffusion coefficient of gas, cm$^2$/sec
G=magnetic field gradient, gauss/cm
J(G)=magnetic field gradient distribution, cm/gauss
γ=proton gyromagnetic ratio,=2π*4258/gauss-sec.

The functions $F(t, D_{oil})$ and $F(t, D_{gas})$ are determined by mapping the magnetic field of the logging device and obtaining the distribution of the gradients of the magnetic field over the measurement region, and by numerically integrating with appropriate weighting for measurement sensitivity. A more direct determination can be achieved by a measurement with the logging tool using a large water bottle spanning the sensitive region of investigation, and using a long echo spacing (e.g. 2 ms). Reference can be made to the publication of C. Flaum et al., supra. With this approach, the value of the integral for any $T_E$ and D can be obtained from the above measurement by a simple dependent variable transformation from "t" to "$DT_E^2t$".

In one embodiment hereof, pulse sequences are applied at a first relatively short wait time, $T_{W1}$, and a second relatively long wait time $T_{W2}$, and echo differences are obtained. $T_{W1}$ is chosen to be long enough to completely polarize the water, but short enough to polarize the hydrocarbon as little as possible. $T_{W2}$ is chosen to polarize all fluids as much as possible. In a typical practical situation, $T_{W1}$ may be about 1 s, and $T_{W2}$ about 4 s. Since the water is fully polarized in both cases, its contribution is eliminated in the echo difference. Since the amount of polarization of the hydrocarbons is different for the two wait times, the difference signal will contain only hydrocarbon contribution.

The echo difference signal is then fitted to a linear combination of the two response functions, one for oil and the other for gas. This fitting can be performed by a well known Weighted Least Squares procedure. The two coefficients resulting for the fit will indicate the corresponding volumes of oil and gas. It will be understood that other suitable methods of fitting to the response functions could be employed.

In a further embodiment hereof the echo spacing can be varied (instead of, or in addition to) varying the wait times, and a train of differences of corresponding echoes can be processed in a similar fashion. Some interpolation and/or decimation will be necessary to produce the two echo trains at the same time samples, so that a difference can be obtained. [Reference can be made, for example, to the publication of C. Flaum et al., supra, and to the above-referenced copending U.S. patent application Ser. No. 08/873,582.] In the simplest version of this embodiment, the wait time $T_W$ is the same for both sets, and two echo spacings, $T_{E-long}$ and $T_{E-short}$ are employed. In this case, a new variable $T_E$ needs to be introduced into the diffusion integrals $F(t,D,T_E)$ of eq. (6), and, since the water signal is not always eliminated, water integrals also need to be computed. Following the same approach of employing the integrals F, the three response functions can be obtained using the equations below:

$$f(t)_{oil} = (1-e^{-T_W/T_{1-oil}})e^{-t/T_{2-oil}}[F(t, D_{oil}, T_{E-short})-F(t, D_{oil}, T_{E-long})] \quad (7a)$$

$$f(t)_{gas} = HI_{gas}(1-e^{-T_W/T_{1-gas}})e^{-t/T_{2-gas}}[F(t, D_{gas},T_{E-short})-F(t,D_{gas}, T_{E-long})] \quad (7b)$$

$$f(t)_{water} = (1-e^{-T_W/T_{1-water}})e^{-t/T_{2-water}}[F(t, D_{water},T_{E-short})-F(t,D_{water}, T_{E-long})] \quad (7c)$$

In this case, the equations for the function F [like (6a) and (6b) above, but with $T_E$ now a variable] will be of the form $$F(t,D_{oil},T_{Eshort}) = \int J(G)e^{-(G^2\gamma^2T^2Eshort^{Doil/12})}dG \quad (8a)$$

$$F(t,D_{oil},T_{Elong}) = \int J(G)e^{-(G^2\gamma^2T^2Elong^{Doil/12})}dG \quad (8b)$$

$$F(t,D_{gas},T_{Eshort}) = \int J(G)e^{-(G^2\gamma^2T^2Eshort^{Dgas/12})}dG \quad (8c)$$

$$F(t,D_{gas},T_{Elong}) = \int J(G)e^{-(G^2\gamma^2T^2Elong^{Dgas/12})}dG \quad (8d)$$

$$F(t,D_{water},T_{Eshort}) = \int J(G)e^{-(G^2\gamma^2T^2Eshort^{Dwater/12})}dG \quad (8e)$$

$$F(t,D_{water},T_{Elong}) = \int J(G)e^{-(G^2\gamma^2T^2Elong^{Dwater/12})}dG \quad (8f)$$

The echo spacings are chosen to provide maximum contrast in diffusion effect, without unduly degrading the signal-to-noise ratio of the long echo spacing data. For example, 0.25 ms and 1 ms, respectively, can be used.

The difference signal can be fitted to a linear combination of the three functions above, to obtain oil, gas and water volumes.

In many practical situations, the oil and water signals may be too similar to be accurately distinguishable. This is not a limitation, since determination of gas volume is the most important goal of this measurement. In many practical situations the echo difference can be fitted to either gas and oil or gas and water pairs of response functions. In general, this embodiment is more sensitive to the difference between the behavior of gas and liquids than is the embodiment first set forth.

In a further embodiment hereof, the measured echo amplitudes can be modified using the previously set forth equation (5)

$$A^*(t) = A(t)/F(t,D_{gas}) \quad (5)$$

and transformed into $T_2$ space. It can then be seen from eq. (4), that the gas phase will now appear as a narrow peak in the $T_2$ distribution, at its bulk value. Because the oil phase has a much lower diffusion coefficient, D, the oil signal will be pushed into much higher $T_2$ values by this transformation, thereby separating it from the gas signal, so that the presence or absence of gas can be detected.

Figure 7A:
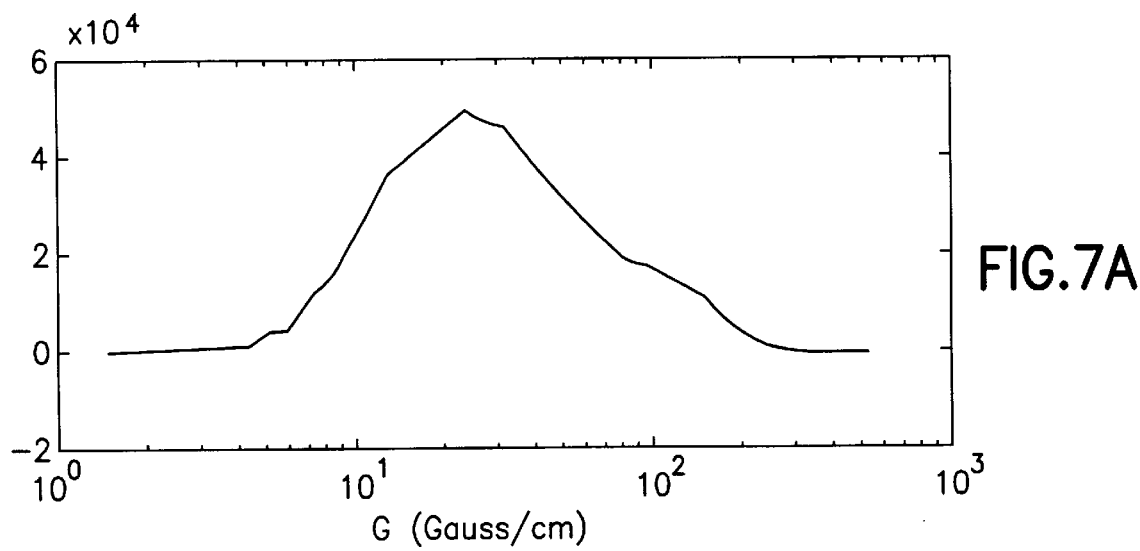
FIG. 7 is an example of gradient field distribution of the static magnetic field.
Figure 7B:
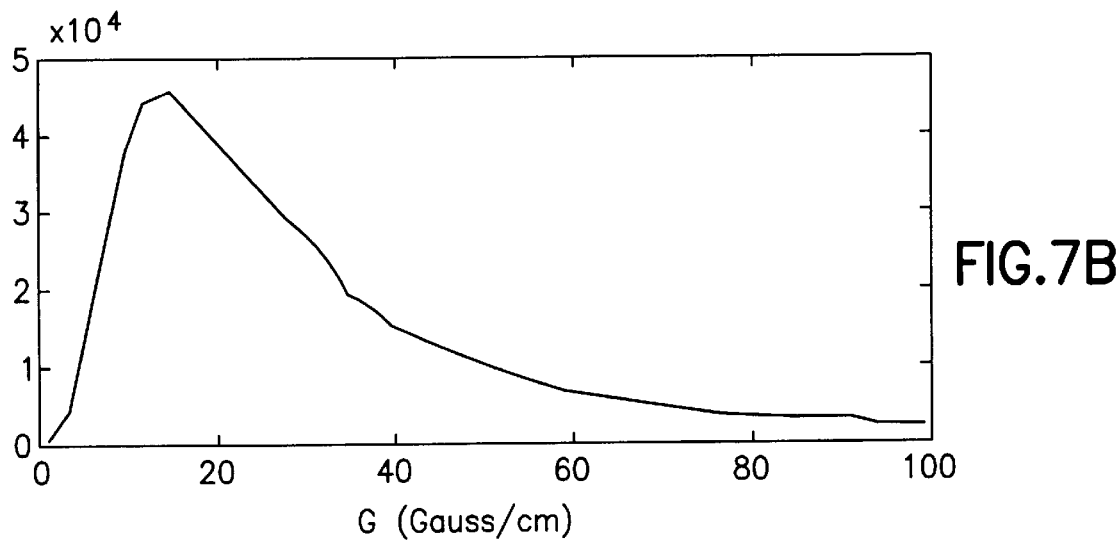
Figure 7C:
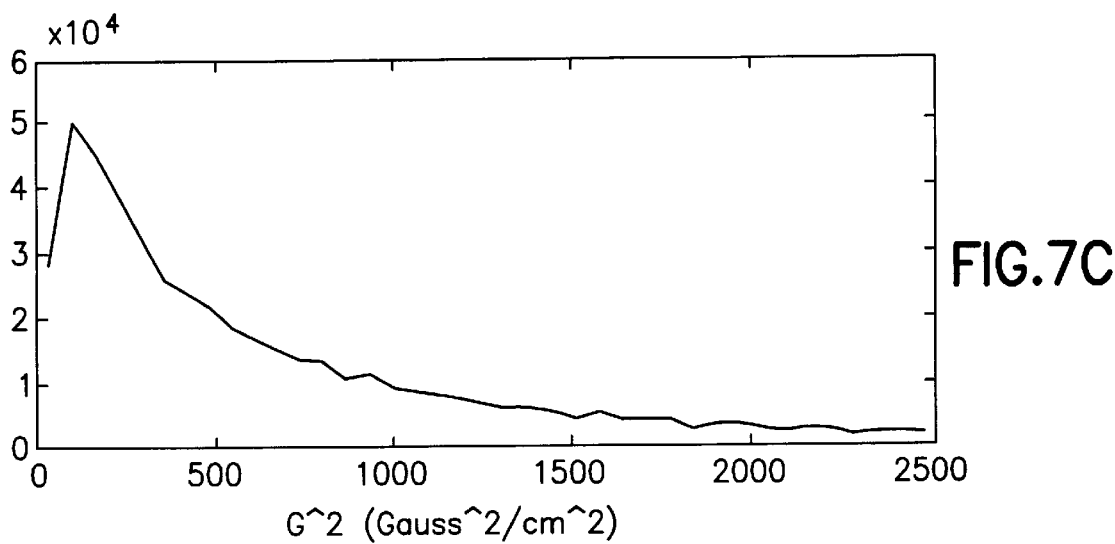

FIG. 7 shows an example of the distribution of static magnetic field gradients (taking into account the tool sensitivity in the investigation region) in the investigation region of the logging tool. The graph 7A is on a logarithmic scale of G (in Gauss/cm), whereas the graph 7B in on a linear scale of G (again in Gauss/cm). The graph 7C is on a linear scale of $G^2$ (in Gauss$^2$/cm$^2$).

Figure 8A:
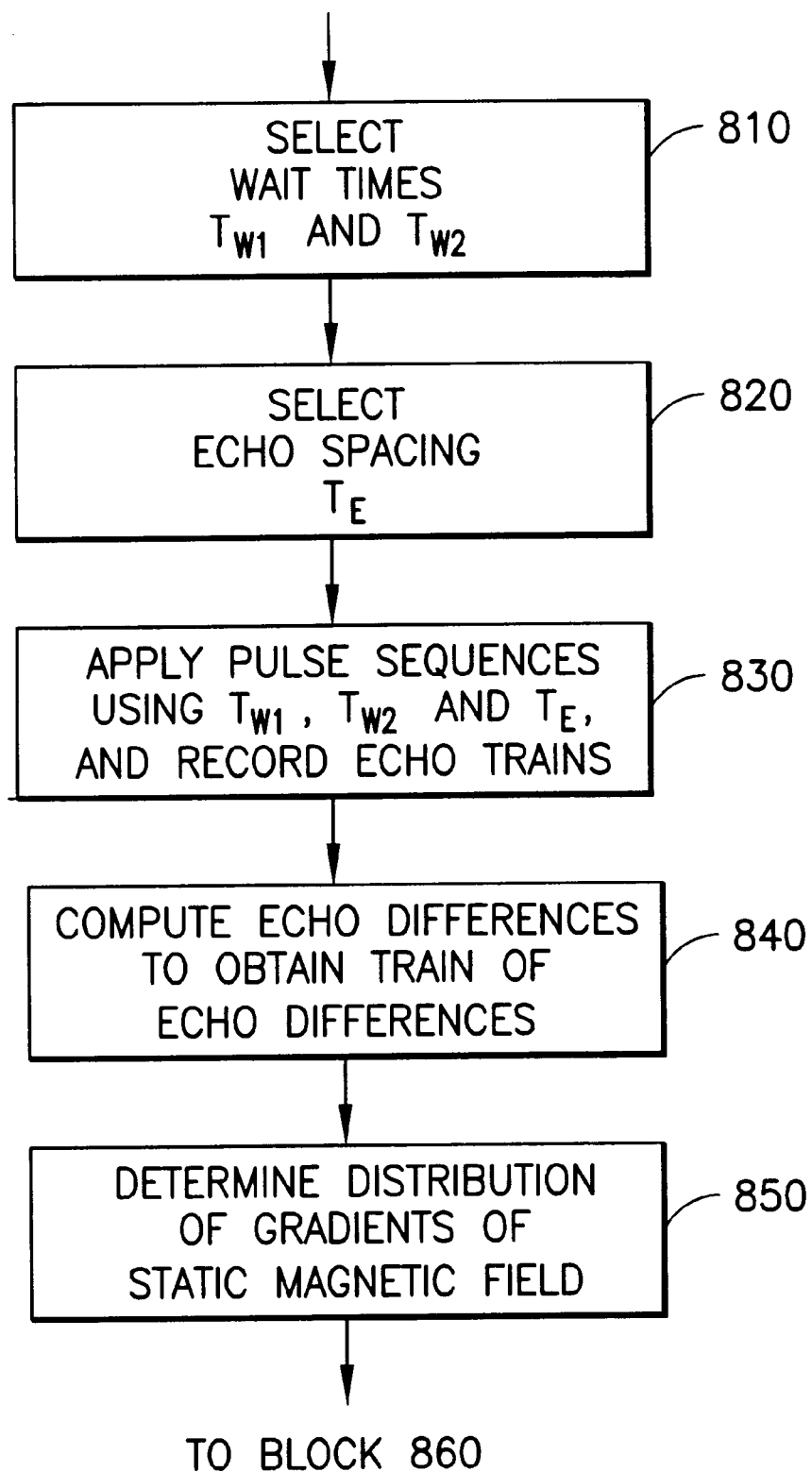
FIG. 8, which includes FIGS. 8A and 8B placed one below another, is a flow diagram of a routine for controlling a processor subsystem in accordance with an embodiment of the invention.
Figure 8B:
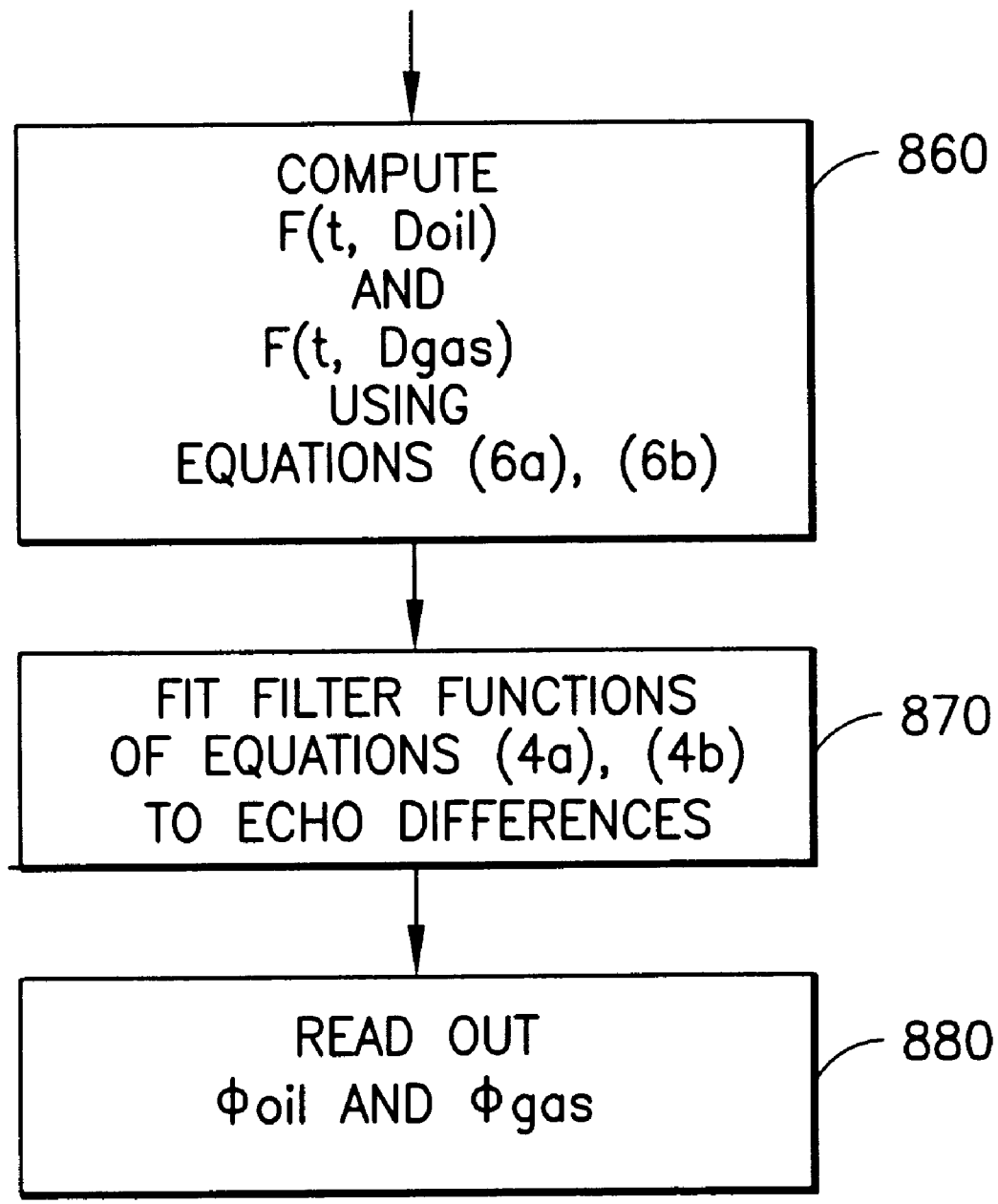

Referring to FIG. 8, there is shown a flow diagram of a routine for controlling a processor in accordance with an embodiment of the invention. The processor can be the downhole processor, the uphole processor, or a remote processor which operates subsequently on stored and/or transmitted log-representative signals, as well as combinations of downhole, uphole, and remote processors. In the flow diagram of FIG. 8, the block 810 represents selecting of wait times $T_{W1}$ and $T_{W2}$. $T_{W1}$ will be substantially longer than $T_{W2}$. For example, in an illustrative embodiment hereof, $T_{W1}$ can be 1 s and $T_{W2}$ can be 4 s. Next, as represented by the block 820, $T_E$, the echo spacing, is selected for the pulse sequence. [The present embodiment can be practiced without varying $T_E$.] Next, as represented by the block 830, pulse sequences are applied with wait times $T_{W1}$ and $T_{W2}$ (both with the $T_E$ that was selected), and the resultant echo trains are recorded. It will be understood that any suitable technique can be used for applying the pulse sequences; for example, they can be applied sequentially or can be applied simultaneously using known multiplexing techniques. The differences of corresponding echoes from the two echo trains are then computed to obtain a train of echo differences (block 840). The distribution of gradients of the static magnetic field (e.g. FIG. 7) is then determined, as represented by the block 850. Then, as described above, the functions $F(t,D_{oil})$ and $F(t,D_{gas})$ are computed, using equations (6a) and (6b) (block 860). The response functions [of equations (4a) and (4b)] are then fit to the train of echo differences, to obtain the weighting coefficients for the best fit (block 870), and the porosities $\Phi_{oil}$ and $\Phi_{gas}$ are read out (block 880). In some instances, only the volume of gas may be utilized.

Figure 9A:
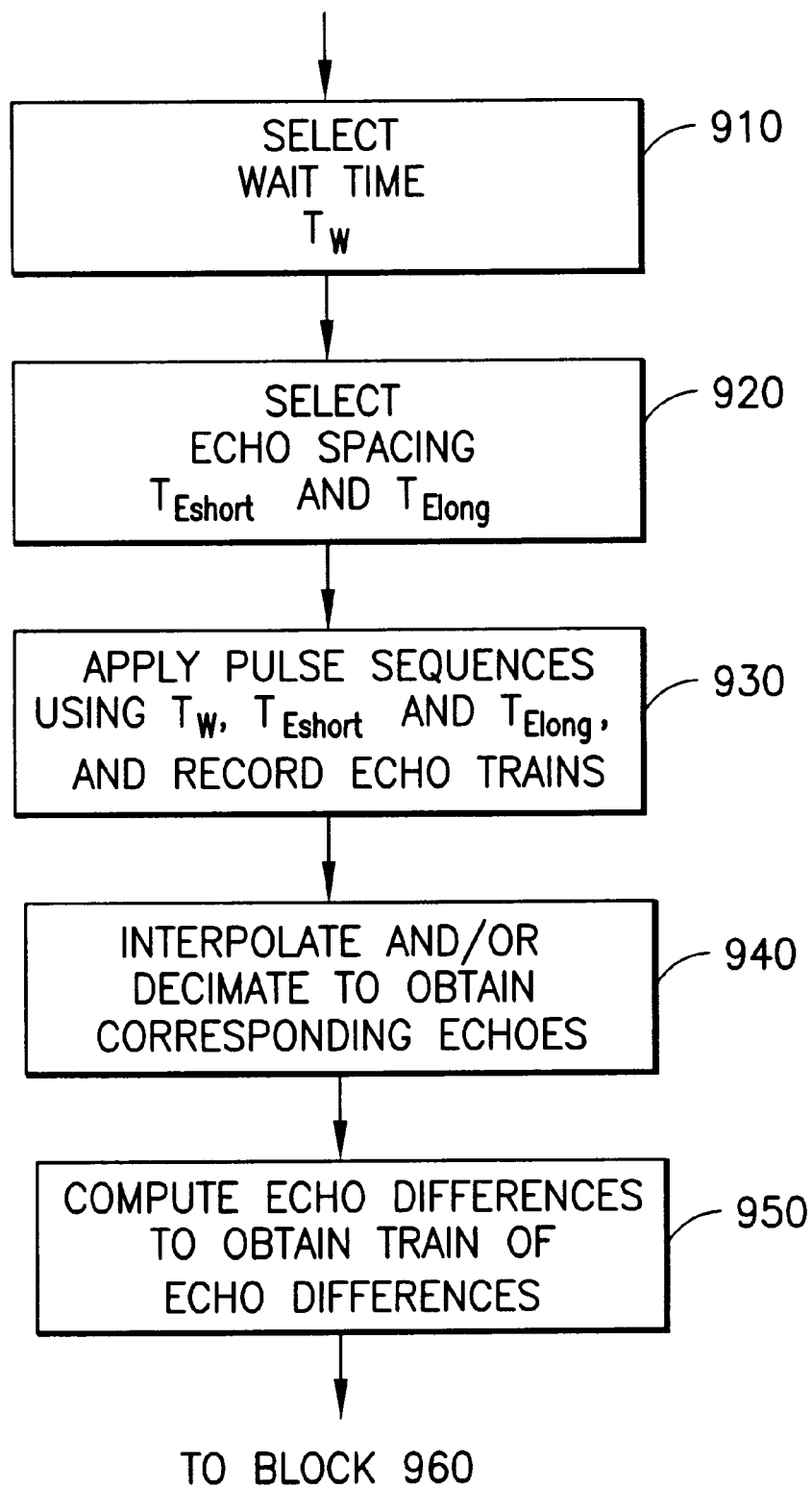
FIG. 9 is a flow diagram of a routine for controlling a processor subsystem in accordance with another embodiment of the invention.
Figure 9B:
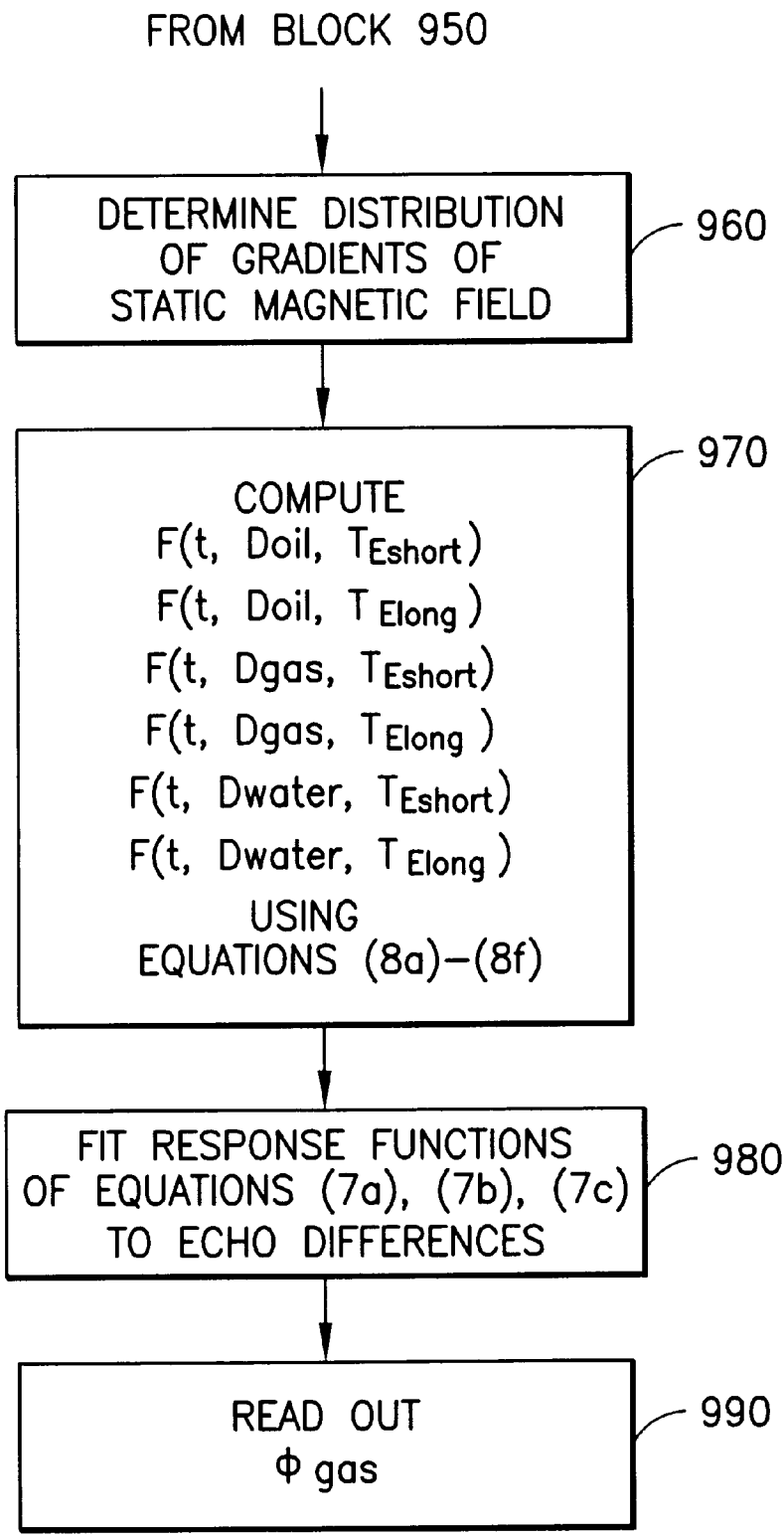

FIG. 9 is a flow diagram of a routine for controlling the processor in accordance with further embodiment described above wherein the echo spacing is varied. The wait time $T_W$ (e.g. 1.5 seconds) and the echo spacings $TE_{short}$ and $TE_{long}$ are selected (blocks 910 and 920). Then, as previously described, interpolation and/or decimation (block 940) is followed by computation of echo differences to obtain a train of echo differences (block 950). As before, the distribution of gradients of the magnetic field is determined (block 960). The six functions of equations (8a)–(8f), namely $F(t,D_{oil}, T_{Eshort})$ $F(t, D_{oil}, T_{Elong})$, $F(t,D_{gas}, T_{Ehort})$, $F(t,D_{gas}, T_{Elong})$, $F(t,D_{water}, T_{Ehort})$, and $F(t,D_{water}, T_{Elong})$ are then computed, for example by using the time transformation referenced above. The response functions of equations (7a), (7b), and (7c) are then fit to the echo difference signal (block 980) and the volume of gas is read out (block 990). The volume of water and oil can also be read out, if deemed useful in the particular application.

Figure 10:
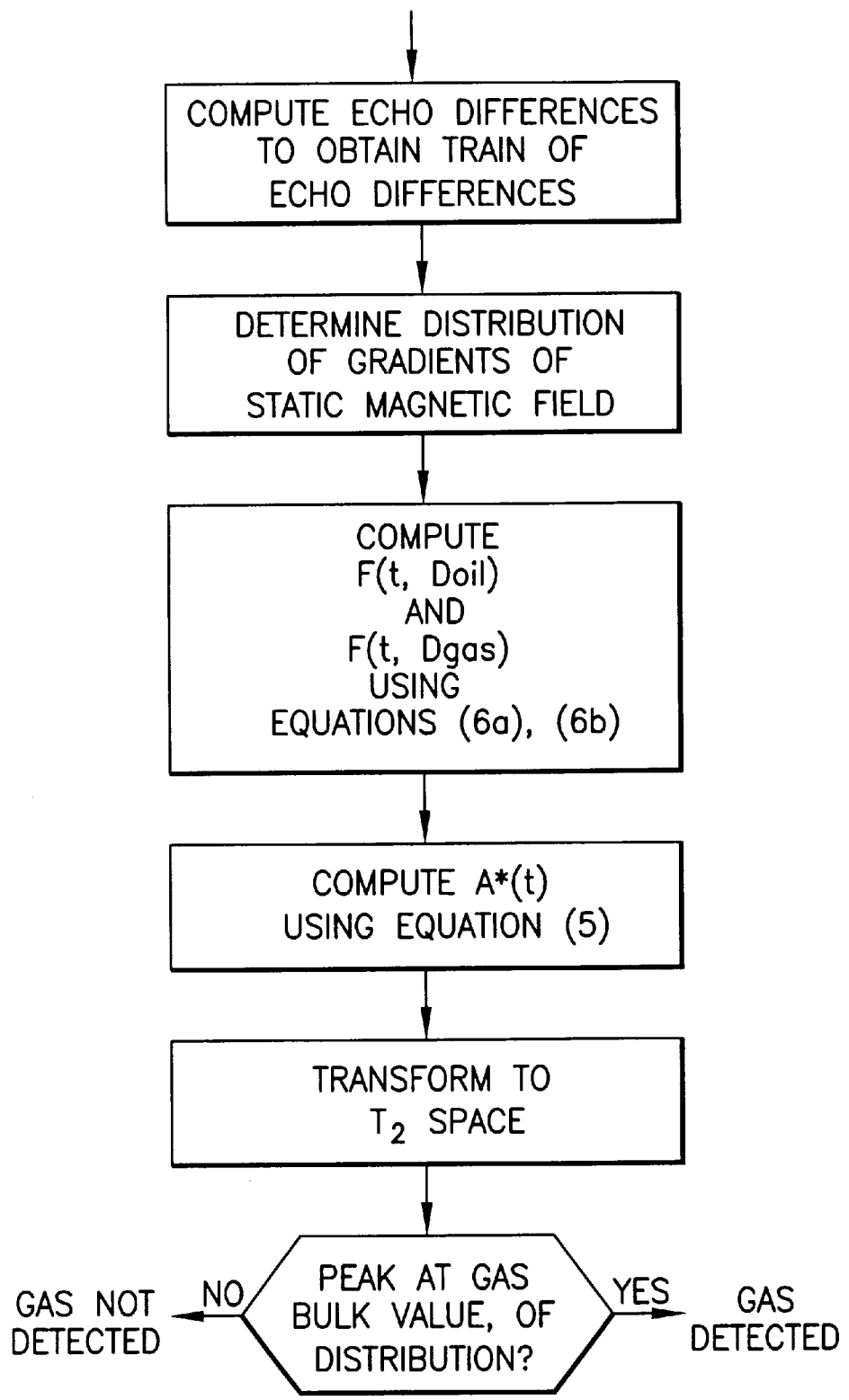
FIG. 10 is a flow diagram of a routine for controlling a processor subsystem in accordance with another embodiment of the invention.

FIG. 10 is a flow diagram of a routine for controlling the processor in accordance with a further embodiment of the invention for detecting the presence of gas in the investigation region. The block 840 represents, for example, the corresponding block of FIG. 8A of computing echo differences to obtain a train of echo differences, it being assumed that the previous portions of the FIG. 8A routine have been already implemented. The block 1005 represents the determination of the distribution of gradients of the static magnetic field, as above, and the block 1010 represents determination of the functions $F(t,D_{oil})$ and $F(t,D_{gas})$, using equations (6a) and (6b) as first described above in conjunction with block 860 of FIG. 8B. The modified amplitudes $A^*(t)$ are then computed using equation (5) (block 1020). Transformation to $T_2$ space is then implemented, as represented by the block 1030. In this regard, reference can be made, for example, to R. Freedman et al., "Processing Of Data From An NMR Logging Tool", SPE 30560, 1995, and to E. Fordham et al., "Imaging Multiexponential Relaxation In the (y, log$T_1$) Plane", Journal Of Magnetic Resonance, 1995, and to U.S. Pat. No. 5,291,137. A determination can then be made (decision block 1050) as to whether there is a peak at the gas bulk value in the distribution. If so, the presence of gas has been detected and, if not, the opposite conclusion is drawn.

What is claimed is:

1. A method for determining the gas-filled porosity and oil-filled porosity in a region of investigation of earth formations surrounding a borehole, comprising the steps of:

a) providing a logging device that is moveable through the borehole;

b) generating, from said logging device, a static magnetic field in the region of investigation of the formations, said static field having a magnetic field gradient that is not constant in said region of investigation;

c) determining the gradient distribution of said static magnetic field in said region of investigation, and determining a first function of said gradient distribution and the diffusion coefficient of oil, and a second function of said gradient distribution and the diffusion coefficient of gas;

d) generating, from said logging device, a first sequence of magnetic field pulses in the region of investigation of the formations using a first wait time, and detecting a first sequence of nuclear magnetic resonance spin echoes from the formations;

e) generating, from said logging device, a second sequence of magnetic field pulses in the region of investigation of the formations using a second wait time, and detecting a second sequence of nuclear magnetic resonance spin echoes from the formations;

f) producing, from differences of respective echoes of said second and first sequences of spin echoes, an echo difference signal; and g) determining the gas-filled porosity and oil-filled porosity in said region of investigation of earth formations from: said echo difference signal, a response function which depends on said first function, and a response function which depends on said second function.

2. The method as defined by claim 1, wherein said first wait time is a relatively short wait time, and said second wait time is a relatively long wait time.

3. The method as defined by claim 2, wherein said second wait time is more than twice said first wait time.

4. The method as defined by claim 2, wherein said step of determining gas-filled porosity and oil-filled porosity comprises fitting said echo difference signal to said response function which depends on said second function and said response function which depends on said first function.

5. The method as defined by claim 3, wherein said step of determining gas-filled porosity and oil-filled porosity comprises fitting said echo difference signal to said response function which depends on said second function and said response function which depends on said first function.

6. The method as defined by claim 2, wherein said response function which depends on said first function also depends on the spin lattice relaxation time of bulk oil, and said response function which depends on said second function also depends on the spin lattice relaxation time of bulk gas.

7. The method as defined by claim 4, wherein said response function which depends on said first function also depends on the spin lattice relaxation time of bulk oil, and said response function which depends on said second function also depends on the spin lattice relaxation time of bulk gas.

8. The method as defined by claim 1, wherein said first and second functions are each determined using empirical measurements and a transformation.

9. A method for detecting the presence of gas in a region of investigation of earth formations surrounding a borehole, comprising the steps of:

a) providing a logging device that is moveable through the borehole;

b) generating, from said logging device, a static magnetic field in the region of investigation of the formations, said static field having a magnetic field gradient that is not constant in said region of investigation;

c) determining the gradient distribution of said static magnetic field in said region of investigation, and determining a first function of said gradient distribution and the diffusion coefficient of gas;

d) generating, from said logging device, a first sequence of magnetic field pulses in the region of investigation of the formations using a first wait time, and detecting a first sequence of nuclear magnetic resonance spin echoes from the formations;

e) generating, from said logging device, a second sequence of magnetic field pulses in the region of investigation of the formations using a second wait time, and detecting a second sequence of nuclear magnetic resonance spin echoes from the formations;

f) producing, from differences of respective echoes of said first and second sequences of spin echoes, an echo difference signal;

g) modifying said echo difference signal with said first function to produce a modified echo difference signal;

h) converting said modified echo difference signal into a $T_2$ distribution, where $T_2$ is spin-spin relaxation time; and i) detecting the presence of gas in said region of investigation of earth formations from said $T_2$ distribution.

10. The method as defined by claim 9, wherein said step of modifying said echo difference signal with said first function comprises dividing said difference signal by said first function.

11. The method as defined by claim 10, wherein said first wait time is a relatively short wait time, and said second wait time is a relatively long wait time.

12. The method as defined by claim 11, wherein said second wait time more than twice said first wait time.

13. The method as defined by claim 9, wherein said first and second functions are each determined using empirical measurements and a transformation.

14. A method for determining the gas-filled porosity in a region of investigation of earth formations surrounding a borehole, comprising the steps of:

a) providing a logging device that is moveable through the borehole;

b) generating, from said logging device, a static magnetic field in the region of investigation of the formations, said static field having a magnetic field gradient that is not constant in said region of investigation;

c) generating, from said logging device, a first sequence of magnetic field pulses in the region of investigation of the formations using a first echo spacing, and detecting a first sequence of nuclear magnetic resonance spin echoes from the formations;

d) generating, from said logging device, a second sequence of magnetic field pulses in the region of investigation of the formations using a second echo spacing, and detecting a second sequence of nuclear magnetic resonance spin echoes from the formations;

e) producing, from differences of respective echoes of said first and second sequences of spin echoes, an echo difference signal;

f) determining the gradient distribution of said static magnetic field in said region of investigation, and determining a first pair of functions of said gradient distribution, the diffusion coefficient of oil, and said first and second echo spacings, and a second pair of functions of said gradient distribution, the diffusion coefficient of gas, and said first and second echo spacings; and g) determining the gas-filled porosity in said region of investigation of earth formations from: said echo difference signal, a response function which depends on said first pair of functions, and a response function which depends on said second pair of functions.

15. The method as defined by claim 14, wherein said first echo spacing is relatively short, and said second echo spacing is relatively long.

16. The method as defined by claim 14, wherein said first pair of functions and said second pair of functions are determined using empirical measurements and a transformation.

17. The method as defined by claim 15, wherein said step (f) further comprises determining a third pair of functions of said gradient distribution, the diffusion coefficient of water, and said first and second echo spacings; and wherein said gas filled porosity is determined also from a response function which depends on said third pair of functions.

18. The method as defined by claim 17, wherein said step of determining gas-filled porosity comprises fitting said echo difference signal to: said response function which depends on said first pair of functions, said response function which depends on said second pair of functions, and said response function which depends on said third pair of functions.

19. A method for determining the gas-filled porosity in a region of investigation of earth formations surrounding a borehole, comprising the steps of:

a) providing a logging device that is moveable through the borehole;

b) generating, from said logging device, a static magnetic field in the region of investigation of the formations, said static field having a magnetic field gradient that is not constant in said region of investigation;

c) determining the gradient distribution of said static magnetic field in said region of investigation, and determining a first function of said gradient distribution and the diffusion coefficient of oil, and a second function of said gradient distribution and the diffusion coefficient of gas;

d) generating, from said logging device, a first sequence of magnetic field pulses in the region of investigation of the formations using a first wait time, and detecting a first sequence of nuclear magnetic resonance spin echoes from the formations;

e) generating, from said logging device, a second sequence of magnetic field pulses in the region of investigation of the formations using a second wait time, and detecting a second sequence of nuclear magnetic resonance spin echoes from the formations;

f) producing, from differences of respective echoes of said second and first sequences of spin echoes, an echo difference signal; and g) determining the gas-filled porosity in said region of investigation of earth formations from: said echo difference signal, a response function which depends on said first function, and a response function which depends on said second function.

20. The method as defined by claim 19, wherein said first wait time is a relatively short wait time, and said second wait time is a relatively long wait time.

21. The method as defined by claim 20, wherein said second wait time is more than twice said first wait time.

22. The method as defined by claim 20, wherein said step of determining gas-filled porosity comprises fitting said echo difference signal to said response function which depends on said second function and said response function which depends on said first function.

23. The method as defined by claim 20, wherein said response function which depends on said first function also depends on the spin lattice relaxation time of bulk oil, and said response function which depends on said second function also depends on the spin lattice relaxation time of bulk gas.

24. A nuclear magnetic resonance logging system for determining the gas-filled porosity and oil-filled porosity in a region of investigation of earth formations surrounding a borehole, comprising:

a logging device that is moveable through the borehole;

means in said logging device, for generating a static magnetic field in the region of investigation of the formations, said static field having a magnetic field gradient that is not constant in said region of investigation;

means for determining the gradient distribution of said static magnetic field in said region of investigation, and for determining a first function of said gradient distribution and the diffusion coefficient of oil, and a second function of said gradient distribution and the diffusion coefficient of gas;

means, in said logging device, for generating a first sequence of magnetic field pulses in the region of investigation of the formations using a first wait time, and for detecting a first sequence of nuclear magnetic resonance spin echoes from the formations;

means, in said logging device, for generating a second sequence of magnetic field pulses in the region of investigation of the formations using a second wait time, and for detecting a second sequence of nuclear magnetic resonance spin echoes from the formations;

means for producing, from differences of respective echoes of said second and first sequences of spin echoes, an echo difference signal; and means for determining the gas-filled porosity and oil-filled porosity in said region of investigation of earth formations from: said echo difference signal, a response function which depends on said first function, and a response function which depends on said second function.

25. The system as defined by claim 24, wherein said first wait time is a relatively short wait time, and said second wait time is a relatively long wait time.

26. The system as defined by claim 25, wherein said second wait time is more than twice said first wait time.

27. The system as defined by claim 25, wherein said means for determining gas-filled porosity and oil-filled porosity comprises means for fitting said echo difference signal to said response function which depends on said second function and said response function which depends on said first function.

28. A nuclear magnetic resonance logging system for detecting the presence of gas in a region of investigation of earth formations surrounding a borehole, comprising:
  a logging device that is moveable through the borehole;
  means in said logging device, for generating a static magnetic field in the region of investigation of the formations, said static field having a magnetic field gradient that is not constant in said region of investigation;
  means for determining the gradient distribution of said static magnetic field in said region of investigation, and for determining a first function of said gradient distribution and the diffusion coefficient of gas;
  means in said logging device, for generating a first sequence of magnetic field pulses in the region of investigation of the formations using a first wait time, and for detecting a first sequence of nuclear magnetic resonance spin echoes from the formations;
  means in said logging device, for generating a second sequence of magnetic field pulses in the region of investigation of the formations using a second wait time, and for detecting a second sequence of nuclear magnetic resonance spin echoes from the formations;
  means for producing, from differences of respective echoes of said first and second sequences of spin echoes, an echo difference signal;
  means for modifying said echo difference signal with said first function to produce a modified echo difference signal; and
  means for converting said modified echo difference signal into a $T_2$ distribution, where $T_2$ is spin-spin relaxation time; said $T_2$ distribution being indicative of the presence or absence of gas in said region of investigation of earth formations.

29. The system as defined by claim 28, wherein said means for modifying said echo difference signal with said first function comprises means for dividing said difference signal by said first function.

30. The system as defined by claim 29, wherein said first wait time is a relatively short wait time, and said second wait time is a relatively long wait time.

31. A nuclear magnetic resonance logging system for determining the gas-filled porosity in a region of investigation of earth formations surrounding a borehole, comprising:
  a logging device that is moveable through the borehole;
  means in said logging device, for generating a static magnetic field in the region of investigation of the formations, said static field having a magnetic field gradient that is not constant in said region of investigation;
  means in said logging device, for generating a first sequence of magnetic field pulses in the region of investigation of the formations using a first echo spacing, and for detecting a first sequence of nuclear magnetic resonance spin echoes from the formations;
  means in said logging device, for generating a second sequence of magnetic field pulses in the region of investigation of the formations using a second echo spacing, and detecting a second sequence of nuclear magnetic resonance spin echoes from the formations;
  means for producing, from differences of respective echoes of said first and second sequences of spin echoes, an echo difference signal;
  means for determining the gradient distribution of said static magnetic field in said region of investigation, and for determining a first pair of functions of said gradient distribution, the diffusion coefficient of oil, and said first and second echo spacings, and a second pair of functions of said gradient distribution, the diffusion coefficient of gas, and said first and second echo spacings; and
  means for determining the gas-filled porosity in said region of investigation of earth formations from: said echo difference signal, a response function which depends on said first pair of functions, and a response function which depends on said second pair of functions.

32. The system as defined by claim 24, wherein said first echo spacing is relatively short, and said second echo spacing is relatively long.

33. The system as defined by claim 32, further comprising means for determining a third pair of functions of said gradient distribution, the diffusion coefficient of water, and said first and second echo spacings; and wherein said means for determining gas filled porosity is operative to perform said determination also from a response function which depends on said third pair of functions.

34. The system as defined by claim 33, wherein said means for determining gas-filled porosity comprises means for fitting said echo difference signal to: said response function which depends on said first pair of functions, said response function which depends on said second pair of functions, and said response function which depends on said third pair of functions.

35. A method for determining the gas-filled porosity in a region of investigation of earth formations surrounding a borehole, comprising the steps of:
  a) providing a logging device that is moveable through the borehole;
  b) generating, from said logging device, a static magnetic field in the region of investigation of the formations, said static field having a magnetic field gradient that is not constant in said region of investigation;
  c) generating, from said logging device, a first sequence of magnetic field pulses in the region of investigation of the formations using a first echo spacing, and detecting a first sequence of nuclear magnetic resonance spin echoes from the formations;
  d) generating, from said logging device, a second sequence of magnetic field pulses in the region of investigation of the formations using a second echo spacing, and detecting a second sequence of nuclear magnetic resonance spin echoes from the formations;
  e) producing, from differences of respective echoes of said first and second sequences of spin echoes, an echo difference signal;
  f) determining the gradient distribution of said static magnetic field in said region of investigation, and determining a first pair of functions of said gradient distribution, the diffusion coefficient of water, and said first and second echo spacings, and a second pair of functions of said gradient distribution, the diffusion coefficient of gas, and said first and second echo spacings; and g) determining the gas-filled porosity in said region of investigation of earth formations from: said echo difference signal, a response function which depends on said first pair of functions, and a response function which depends on said second pair of functions.

36. The method as defined by claim 35, wherein said first echo spacing is relatively short, and said second echo spacing is relatively long.

37. The method as defined by claim 35, wherein said first pair of functions and said second pair of functions are determined using empirical measurements and a transformation.

38. The method as defined by claim 36, wherein said step (f) further comprises determining a third pair of functions of said gradient distribution, the diffusion coefficient of oil, and said first and second echo spacings; and wherein said gas filled porosity is determined also from a response function which depends on said third pair of functions.

39. The method as defined by claim 38, wherein said step of determining gas-filled porosity comprises fitting said echo difference signal to: said response function which depends on said first pair of functions, said response function which depends on said second pair of functions, and said response function which depends on said third pair of functions.

* * * * *